US006939873B2

(12) United States Patent
Gutman et al.

(10) Patent No.: US 6,939,873 B2
(45) Date of Patent: *Sep. 6, 2005

(54) NON-SEDATING BARBITURIC ACID DERIVATIVES

(75) Inventors: Daniella Gutman, Rishon (IL); Daniel A. Moros, Larchmont, NY (US)

(73) Assignee: Taro Pharmaceuticals Industries Limited, Haifa Bay (IL)

( * ) Notice: Subject to any disclaimer, the term of this patent is extended or adjusted under 35 U.S.C. 154(b) by 112 days.

This patent is subject to a terminal disclaimer.

(21) Appl. No.: 10/354,146

(22) Filed: Jan. 30, 2003

(65) Prior Publication Data

US 2003/0187005 A1 Oct. 2, 2003

Related U.S. Application Data

(63) Continuation-in-part of application No. 10/333,957, filed as application No. PCT/US01/23420 on Jul. 26, 2001, now Pat. No. 6,756,379.
(60) Provisional application No. 60/221,672, filed on Jul. 26, 2000, and provisional application No. 60/352,273, filed on Jan. 30, 2002.

(51) Int. Cl.$^7$ ............................................ A61K 31/515
(52) U.S. Cl. ..................................................... 514/270
(58) Field of Search ........................................ 514/270

(56) References Cited

U.S. PATENT DOCUMENTS

| | | | |
|---|---|---|---|
| 2,673,205 | A | 3/1954 | Hoffmann et al. |
| 4,060,528 | A | 11/1977 | Janssen et al. |
| 4,578,503 | A | 3/1986 | Ishikawa et al. |
| 4,628,056 | A | 12/1986 | Levitt et al. |
| 4,894,459 | A | 1/1990 | Bod et al. |
| 4,914,226 | A | 4/1990 | Di Trapani et al. |
| 5,120,850 | A | 6/1992 | Bod et al. |
| 5,128,477 | A | 7/1992 | Bod et al. |
| 5,750,766 | A | 5/1998 | Krummel et al. |
| 5,756,815 | A | 5/1998 | Knell |
| 5,808,066 | A | 9/1998 | Krummel et al. |
| 6,051,737 | A | 4/2000 | Kim et al. |
| 6,093,820 | A | 7/2000 | Gutman et al. |
| 6,156,925 | A | 12/2000 | Meyer et al. |
| 6,184,238 | B1 | 2/2001 | Takano et al. |
| 6,262,067 | B1 | 7/2001 | Allen et al. |
| 6,372,757 | B1 | 4/2002 | Johns et al. |
| 6,756,379 | B2 * | 6/2004 | Moros et al. ............... 514/270 |

FOREIGN PATENT DOCUMENTS

| | | |
|---|---|---|
| DE | 1939787 | 2/1970 |
| DE | 2622981 A1 | 12/1977 |
| DE | 4028040 A1 | 3/1992 |
| EP | 726252 A1 | 8/1996 |
| EP | 726252 B1 | 8/1996 |
| EP | 1 083 172 A1 | 3/2001 |
| WO | WO 99/18084 | 4/1999 |
| WO | WO 01/79185 A1 | 10/2001 |
| WO | WO 02/007729 A1 | 1/2002 |

OTHER PUBLICATIONS

Thacker et al., "Method for the Determination of 5,5–Diphenylbarbituric Acid and Separation from 1,3–Dimethoxymethyl–5,5–Diphenylbarbituric Acid in Plasma by High Performance Liquid Chromatography," J. Chromatography B, 710:149–155 (1998).

Raines et al., "Conversion of Dimethoxymethyl–Diphenylbarbituric Acid (DMMDPB) to Diphenylbarbituric Acid (DPB) in the Dog," The FASEB J., 13(4):A475, Abstract 394.2 (1999).

Raines et al., "The Effects of 5,5–Diphenylbarbituric Acid on Experimental Seizures in Rats: Correlation between Plasma and Brain Concentrations and Anticonvulsant Activity," Epilepsia, 16:575–581 (1975).

Raines et al., "A Comparison of the Anticonvulsant, Neurotoxic and Lethal Effects of Diphenylbarbituric Acid Phenobarbital and Diphenylhydantoin in the Mouse," J. Pharmacology and Experimental Therapeutics, 186(2):315–322 (1973).

Tagmana et al., Helv. Chim. Acta 35, 1541–1549 (1952).

Salmon–Legagneur et al., "Sur les acides α–phényl α–alcoyl (ou phénoalcoyl) glutariques", Comptes Rendus de l'Académie des Sciences, (Mar. 3, 1952) p. 1060.

Salmon–Legagneur et al., "Recherches dans la série des diacides αα–disubstitués et de leurs dérivés. III. Les acides α–phénol α–alcoyl (ou phénoalcoyl) glutariques et leurs principaux dérivés", Bull. Soc. Chim. France (1953) p. 70.

The Merck Index, 10th Ed., (Merck & Co., Inc., Rahway, NJ) (1983) p. 544 (entry 3697).

Casara et al., "Synthesis of acid stable fluorinated acyclonucleosides as potential antiviral agents," Tetrahedron Letters, 32(31) (1991), pp. 3823–3826.

Foye, "Principles of Medicinal Chemistry," 3rd. ed. (1990) pp 164, 179.

Karger et al., "Methoxymethyl Methanesulfonate, A Novel Active Oxyalkylating Agent, " J. Am. Chem. Soc., 91:5663 (1969).

Sircar, J. Chem. Soc. (1927) 1252–1256.

Gao et al., "Physical Chemical Stability of Warfarin Sodium," AAPS Pharmasci (2001) 3(1) Article 3.

Appendix 1 of U.S.S.N. 60/352,273, filed Jan. 30, 2002: Chemical Derivative Chart (total of 8 pages).

(Continued)

Primary Examiner—Raymond J. Henley, III

(57) ABSTRACT

The present invention relates to novel non-sedating barbituric acid derivatives, pharmaceutical compositions containing them and methods of neuroprotection in cases of cerebral ischemia, head trauma and other acute neurologic injuries, and prevention of resulting neuronal damage. The invention also relates to the use of non-sedating barbituric acid derivatives given in a manner and dosage effective to produce blood levels and brain levels of these drugs and/or their active metabolites sufficient to provide a therapeutic effect.

32 Claims, No Drawings

OTHER PUBLICATIONS

Appendix 2 of U.S.S.N. 60/352,273, filed Jan. 30, 2002: Reference to Chemical Derivatives (total of 3 pages).
Appendix 3 of U.S.S.N. 60/352,273, filed Jan. 30, 2002: CANCERLIT . . . (total of 9 pages).
Appendix 3 of U.S.S.N. 60/352,273, filed Jan. 30, 2002: PubMed search results printout of Jan. 15, 2002 (total of 7 pages).
Appendix 3 of U.S.S.N. 60/352,273, filed Jan. 30, 2002: MEDLINEplus printout of Jan. 15, 2002: Barbituates (Systemic) (total of 14 pages).
PubMed search results printout of Dec. 27, 2002 (total of 3 pages).
Masuda et al., "Relationships Between Plasma Concentrations of Diphenylthydantoin, Phenobarbital, Carbamazepine, and 3–Sulfanoylmethyl– 1, 2–Benzisoxazole (AD–810), a New Anticonvulsant Agent, and Their Anticonvulsant or Neurotoxic Effects in Experimental Animals", Epilepsia, 20, pp. 623–633, (1979).
Bhardwaj et al., "Pentobarbital inhibits extracellular release of dopamine in the ischemic striatum", Journal of Neural Transmission [Gen Sect], 82, pp. 111–117, (1990).
McElvain, "5,5–Diphenylbartintric Acid", 57, pp. 1303–1304, (1935).
Gesson et al., "A practical method for N–alkylation of succinimide and glutarimide", Bull Soc. Chim. Fr. 129, pp. 227–231, (1992).
Kamata et al., "Studies of Antitumor–Active 5–Fluorouracil Derivatives I Synthesis of N–Phtlalidyl 5–Flourouracil Derivatives", Chem. Pharm. Bull, 33 (8), pp. 3160–3175, (1985).
Samour et al., "Anticonvulsants, I. Alkoxymethyl Derivatives of Barbituates and Diphenylhydantoin", Journal of Medicinal Chemistry, 14 (3), pp. 187–189, (1971).
Raines et al., "Differential Selectivity of Several Barbiturates on Experimental Seizures and Neurotoxicity in the Mouse", Epilepsia, 20, pp. 105–113, (1979).
Loudon, "Organic Chemistry", Addison–Wesley (1984), pp. 617, 721–722, 1061–1064, 1086–1088, 1194.
Corkill et al., Surg. Neurol., pp. 147–149 (1976).
Hoff et al., Stroke, 6, pp. 28–33, (1975).
Levy and Brierley, "Delayed pentobarbital administration limits ischemia brain damage in gerbils", Annals of Neurology, 5(1), pp. 59–64, (1979).
Lightfoote et al., Stroke, 8, pp. 627–628, (1977).
Pulsinelli and Brierley, "A new model of bilateral hemospheric ischemia in the unanesthetized rat", Stroke, May—Jun. 10(3), pp. 267–272, (1979).
Raines et al., Epilepsia 1996, 37:Suppl. 5.
Ginsberg, "Animal Models of Global and Focal Cerebral Ischemia," Chapter 34 in Welsh KMA et al., *Primer on Cerebrovascular Diseases*, Academic Press, New York (1997).
Miller, ed., "Stroke Therapy: Basic, preclinical, and clinical directions", Wiley (1999).
Brint et al., "Focal brain ischemia in the rat: Methods for reproducible neocortical infarction using tandem occlusion of the distal middle cerebral and ipsilateral commoa carotid arteries", J. Cerebral Blood Flow Metab., 8, pp. 474–485, (1988).
Garcia et al., "Neurological deficit and extent of neuronal necrosis attributable to middle cerebral artery occlusion in rats, Statistical validation", Stroke, 26(4), pp. 627–634, (1995).
Garcia et al., "Neuronal necrosis after middle cerebral artery occlusion in Wistar rats progresses at different time intervals in the caudoputamen and the cortex", Stroke, 26(4), 636–643 (1995).
Pulsinelli et al., "Temporal profile of neuronal damage in a model of transient forebrain ischemia", Annals of Neurology, May 11(5), 491–498, (1982).
Raines et al., J. Exp. Biol. (Abstracts) Abstract No. 895 (Apr. 14–17, 1996).

* cited by examiner

NON-SEDATING BARBITURIC ACID DERIVATIVES

This Application is a Continuation-In-Part of the U.S. application Ser. No. 10/333,957, filed Jan. 27, 2003, now U.S. Pat. No. 6,756,379, which is a National Stage of International Application No. PCT/US01/23420, filed Jul. 26, 2001, which claims priority to U.S. Provisional Application No. 60/221,672, filed Jul. 26, 2000. This Application also claims the benefit of U.S. Provisional Application No. 60/352,273, filed Jan. 30, 2002.

BACKGROUND OF THE INVENTION

The present invention relates to novel non-sedating barbituric acid derivatives, pharmaceutical compositions containing them and methods of neuroprotection in cases of cerebral ischemia, head trauma and other acute neurologic injuries, and prevention of resulting neuronal damage. The invention also relates to the use of non-sedating barbituric acid derivatives given in a manner and dosage effective to produce blood levels and brain levels of these drugs and/or their active metabolites sufficient to provide a therapeutic effect.

Barbituric acid and its derivatives have been known since the turn of the century to possess pharmacological properties and some of them serve as active ingredients in widely used drugs. Barbituric acid derivatives are known to act mainly as sedatives, hypnotics and anaesthetics. Certain derivatives also have an anticonvulsive effect and are therefore employed in the treatment of epilepsy. Thus, pharmaceutical compositions containing 5-ethyl-5-phenyl barbituric acid (phenobarbital) are at present most widely used as drugs employed in the treatment of epilepsy. However, like other barbituric acid derivatives, phenobarbital has sedative and hypnotic effects, which are a disadvantage in the treatment of epilepsy. Therefore, a great effort has been devoted to the search for compounds which have anticonvulsant properties and at the same time are devoid of sedative and hypnotic effects.

For example, a known derivative of barbituric acid is 5,5-diphenyl barbituric acid, which was disclosed by S. M. McElvain in J. Am. Chem. Soc. 57, 1303 (1935), which is incorporated herein by reference in its entirety. The compound was found to be effective only in very large doses and therefore no pharmacological application was suggested. Raines et al. reported in Epilepsia 20, 105 (1979), which is incorporated herein by reference in its entirety, that 5,5-diphenyl barbituric acid has an anticonvulsant effect on rodents but with the disadvantage of relatively short term activity. Additionally non-sedating barbituric acid derivatives have been disclosed in Levitt, U.S. Pat. No. 4,628,056, and Moros et al., WO 02/007729 A1, published Jan. 31, 2002, each of which is incorporated by reference herein in its entirety.

Ischemia (stroke) is the third leading cause of death in the United States. When blood supply to the brain is reduced below a critical threshold, a cascade of biochemical events leads to irreversible damage to neurons and brain infarction. Research on treatment and prevention of ischemia is extensive but unfortunately it remains at a basic stage and no adequate therapies are yet in practice (Stroke Therapy: Basic clinical and pre-clinical directions, Leonard P. Miller, ed. (Wiley 1999)).

Barbiturates in high concentrations have been shown to be neuroprotective in cerebral ischemia in rodents and primates, to reduce the extent of ischemia brain infarction, and to prevent or lessen brain damage (Hoff J T, Smith A L, Hankinson H L, Nielsen S L, Stroke 1975, 6:28–33; Levy D E, Brierley J B. Delayed pentobarbital administration limits ischemia brain damage in gerbils; Lightfoote W E II, Molinari G F, Chase T N, Stroke 1977, 8:627–628; Corkill G, Chikovani O K, McLeish I, McDonald L W, Youmans J R, Surg. Neurol. 1976, 147–149). One theory as to how barbiturates prevent neuronal injury in ischemia is that they inhibit the ischemia-induced uncontrolled release of neurotransmitters, which can attain high, neurotoxic concentrations that cause neuronal death (Bhardwaj A, Brannan T, Weinberger J, J Neural Transom 1990, 82:111–117).

The literature regarding the neuroprotective effects of anesthetic barbiturates is over two decades old, but the clinical use of barbiturates has been severely limited because of toxicity. The dosages and blood and brain levels necessary to confer neuroprotection are toxic and cause lethargy, stupor, and coma. Even higher doses that might be more effective are lethal (Hoff J T, Smith A L, Hankinson H L, Nielsen S L, Stroke 1975, 6:28–33; Levy D E, Brierley J B. Delayed pentobarbital administration limits ischemia brain damage in gerbils; Lightfoote W E II, Molinari G F, Chase T N, Stroke 1977, 8:627–628; Corkill G, Chikovani O K, McLeish I, McDonald L W, Youmans J R, Surg. Neurol. 1976, 147–149; Masuda Y, Utsui Y, Shiraishi Y, Karasawa T, Yoshida K, Shimizu M., Epilepsia 1979, 20:623–633.), making barbiturates unsuitable for treatment of ischemia (Hoff J T, Smith A L, Hankinson H L, Nielsen S L, Stroke 1975, 6:28–33). These toxic side effects establish a "functional ceiling" on dosage for barbiturates, and have discouraged further research into the use of anesthetic/sedative barbiturates to protect from ischemia.

Levitt et al., U.S. Pat. No. 4,628,056 describes non-sedating oxopyrimidine derivatives and their use as anticonvulsants, anti-anxiety and muscle relaxant agents. The literature does not suggest the use of such compounds as neuroprotectant agents. Indeed, even in published studies about using sedative barbiturates for neuroprotection there is no reference to non-sedating barbiturate compounds. It is generally believed that the anticonvulsant and neuroprotective effects of barbiturates are linked to their sedative/hypnotic effects. For example, Lightfoote et al. suggested that the protective effects of pentobarbital are due to the duration of the barbiturate-induced anesthesia (Lightfoote W E II, Molinari G F, Chase T N, Stroke 1977, 8:627–628). This viewpoint has been reinforced by biochemical studies at the cell receptor level that relate all these effects to action at the GABA receptor. Thus, the prior art teaches away from using sedative barbiturates for neuroprotection because of their toxicity, and also teaches away from using non-sedative barbiturates as neuroprotectants because they lack sedating or anesthetic properties.

Some barbituric acid derivatives of Formula I and their methods of preparation are known.

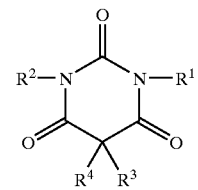

(I)

For example, U.S. Pat. No. 6,093,820, which is incorporated by reference herein in its entirety, describes the synthesis of N,N-bismethoxymethyl-5,5-dipheyl barbitutric acid (Formula I, $R^1=R^2=CH_2OMe$ and $R^3=R^4=Ph$). U.S. Pat. No. 4,628,056, which is incorporated by reference herein in its entirety, describes an alternative synthesis of this compound.

SUMMARY OF THE INVENTION

It is therefore the object of the present invention to provide novel non-sedating barbituric acid derivatives having a long acting neurological activity and being devoid of any significant hypnotic and sedative effects. Neurological activity may include neuroprotective, anti-stress and anti-strain, anticonvulsant, anti-seizure, muscle relaxant, anti-nervous strain, and anti-anxiety.

Non-sedating barbituric acid derivatives, also termed non-sedative barbiturates, of the present invention have the general Formula I

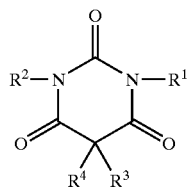

(I)

wherein $R^1$ and $R^2$ may be the same or different and are independently hydrogen;
lower alkyl, optionally substituted by lower cycloalkyl, acyl, acyloxy, aryl, aryloxy, lower alkoxy, thioalkyl or thioaryl, amino, alkylamino, dialkylamino, or one or more halogen atoms;
phenyl;
$CH_2XR^5$, wherein X is S or O and $R^5$ is lower alkyl, aryl, or alkylaryl (e.g., benzyl);
$C(O)XR^6$, wherein X is as defined above and $R^6$ is lower alkyl or aryl;
$CXR^7$, wherein X is as defined above and $R^7$ is hydrogen, lower alkyl or aryl; and
$CH(XR^8)_2$, wherein X is as defined above and $R^8$ is a lower alkyl group, with the proviso that at least one of $R^1$ and $R^2$ is not hydrogen.

$R^3$ and $R^4$ may be the same or different and are independently hydrogen; aryl optionally containing one or more heteroatoms selected from the group consisting of N, S and O; lower acyloxy; phenyl; phenyl substituted with a halogen, lower alkyl group, lower acyl group or derivative thereof or acetamido; benzyl; benzyl substituted on the ring by one or more halogens, lower alkyl groups or both; cycloalkyl, which optionally contains one or more heteroatoms selected from the group consisting of N, O and S; lower alkyl; or lower alkyl substituted with an aromatic moiety. At least one of $R^3$ and $R^4$ is an aromatic ring or an aromatic ring containing moiety. As used herein, lower alkyl refers to a branched or straight chain alkyl group having eight or fewer carbons. Alkyl also includes hydrocarbon groups having one or two double or triple bonds in the chain. The present invention also includes salts of the aforementioned compounds. In the compounds and salts of the present invention, 1. when $R^1$ and/or $R^2$ is methoxymethyl, $R^3$ and $R^4$ are not both phenyl, are not both phenyl substituted by lower alkyl, and are not both phenyl substituted by halogen; and 2. when one of $R^3$ and $R^4$ is phenyl or benzyl, the other of $R^3$ and $R^4$ is not ethyl; and 3. when at least one of $R^1$ and $R^2$ is benzyl, then when one of $R^3$ and $R^4$ is phenyl, the other of $R^3$ and $R^4$ is not allyl; and 4. when one of $R^1$ and $R^2$ is methyl and the other is hydrogen, then when one of $R^3$ and $R^4$ is phenyl, the other of $R^3$ and $R^4$ is not unsubstituted lower alkyl; and 5. when $R^1=R^2=R^a$, where $R^a$ is alkoxymethyl or (acyloxy)methyl, then when one of $R^3$ and $R^4$ is 1-phenylethyl, the other of $R^3$ and $R^4$ is not propionyloxy.

Furthermore, the following compounds are not included within the scope of the present invention with respect to compositions, but can be used in practicing the method of the invention.

a) 1-methyl-5-(1-phenylethyl)-5-propionyloxy-barbituric acid,
b) 1,3-diphenyl-5,5-(dibenzyl) barbituric acid,
c) 1,3,5-triphenyl barbituric acid, and
d) 5-benzyl-1,3-dimethyl barbituric acid.

In some exemplary embodiments, at least one of $R^1$ and $R^2$ is lower alkyl substituted by lower cycloalkyl, acyl, acyloxy, aryl, aryloxy, thioalkyl or thioaryl, amino, alkylamino, dialkylamino, or one or more halogen atoms; phenyl; $CH_2SR^5$, wherein $R^5$ is lower alkyl, aryl, alkylaryl or benzyl; $C(S)XR^6$, wherein X is S or O and $R^6$ is lower alkyl or aryl; $CSR^7$, wherein $R^7$ is hydrogen, lower alkyl or aryl; and $CH(SR^8)_2$, wherein $R^8$ is a lower alkyl group.

In other exemplary embodiments, at least one of $R^3$ and $R^4$ is lower acyloxy; phenyl substituted with a lower acyl group or derivative thereof or acetamide; and cycloalkyl of which the ring optionally contains one or more heteroatoms selected from the group consisting of N, O and S.

In certain exemplary embodiments of the invention, the substituents $R^1$ and $R^2$ are different and are individually selected from butyl, benzyl, thiophenylmethyl, cyclopropylmethyl, 3,3,3-trifluoropropyl, benzyloxymethyl, and alkoxymethyl. In other exemplary embodiments, $R^1$ and $R^2$ are the same and are selected from butyl, benzyl, thiophenylmethyl, cyclopropylmethyl, 3,3,3-trifluoropropyl, benzyloxymethyl, and alkoxymethyl. In other exemplary embodiments, one of $R^1$ and $R^2$ is hydrogen and the other of $R^1$ and $R^2$ is selected from alkoxymethyl, butyl, benzyl, thiophenylmethyl, cyclopropylmethyl, 3,3,3-trifluoropropyl, and benzyloxymethyl.

In other exemplary embodiments, at least one of $R^1$ and $R^2$ are methoxymethyl. In other exemplary embodiments, $R^3$ and $R^4$ are both aromatic rings or aromatic ring containing moieties.

In certain exemplary embodiments, $R^3$ and $R^4$ are the same or different and are independently phenyl; phenyl substituted with a halogen or lower alkyl group; cycloalkyl, which optionally contains one or more heteroatoms selected from the group consisting of N, O and S; benzyl; benzyl substituted on the ring by one or more halogens, lower alkyl groups or both; lower alkyl; or lower alkyl substituted with an aromatic moiety, provided that at least one of $R^3$ and $R^4$ is phenyl or substituted phenyl.

In other exemplary embodiments, at least one of $R^3$ and $R^4$ are selected from the group consisting of phenyl, benzyl, fluorophenyl and tolyl.

In other exemplary embodiments, at least one of $R^3$ and $R^4$ is selected from:

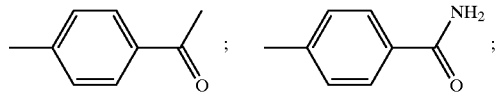

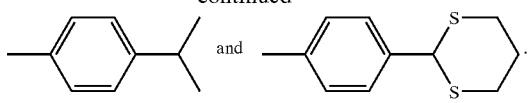

R³ and R⁴ may be the same or different.

Non-sedating barbituric acid derivatives according to the invention may be administered to treat mammals for strain and stress conditions and nervous dysfunctions such as convulsions, seizure, muscle stiffness, nervous strain and anxiety. Non-sedating barbituric acid derivatives according to the invention may also be administered to achieve a neuroprotective effect.

The present invention also encompasses pharmaceutical compositions having a compound of Formula I as the active ingredient together with a pharmaceutically acceptable carrier.

The invention further provides an article of manufacture comprising a container comprising a pharmaceutical composition and a label with indications for use as a treatment for strain and stress conditions; nervous dysfunctions such as convulsions, seizure, muscle stiffness, nervous strain and anxiety, and/or as a neuroprotectant, the pharmaceutical composition comprising a non-sedating barbiturate compound in a pharmacologically effective amount together with a pharmaceutically acceptable carrier or excipient.

DETAILED DESCRIPTION

In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The above-described embodiments of the invention may be modified or varied, and elements added or omitted, without departing from the invention, as appreciated by those skilled in the art in light of the above teachings. Each reference cited here is incorporated by reference as if each were individually incorporated by reference.

Levitt et al., U.S. Pat. No. 4,628,056, describes non-sedating oxopyrimidine derivatives and their use as anticonvulsants, anti-anxiety and muscle relaxant agents. Levitt further describes the preparation of some 1,3-disubstituted-5,5-diphenyl barbituric acid derivatives. The diphenyl substituents of Levitt may be further substituted by lower alkyl or halogen. Gutman et al., U.S. Pat. No. 6,093,820, describes methods of N-alkylating ureides that are useful for preparing mono- and di-N substituted barbituric acid derivatives. The methods disclosed can be useful in preparing compounds useful in the present invention. Moros et al., WO 02/007729 A1, incorporated herein by reference in its entirety, describes the use of non-sedating barbiturate compounds as neuroprotective agents.

The term "non-sedative barbituric acid derivatives" as used herein encompasses the family of barbituric acid anticonvulsant compounds and derivatives and structural analogs having the general Formula I, and salts thereof

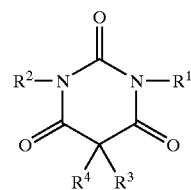

wherein R¹ and R² may be the same or different and are independently hydrogen;

lower alkyl, optionally substituted by lower cycloalkyl, acyl, acyloxy, aryl, aryloxy, lower alkoxy, thioalkyl or thioaryl, amino, alkylamino, dialkylamino, or one or more halogen atoms;

phenyl;

$CH_2XR^5$, wherein X is S or O and $R^5$ is lower alkyl, aryl, or alkylaryl (e.g., benzyl);

$C(O)XR^6$, wherein X is as defined above and $R^6$ is lower alkyl or aryl;

$CXR^7$, wherein X is as defined above and $R^7$ is hydrogen, lower alkyl or aryl; and $CH(XR^8)_2$, wherein X is as defined above and $R^8$ is a lower alkyl group, with the proviso that at least one of $R^1$ and $R^2$ is not hydrogen.

$R^3$ and $R^4$ may be the same or different and are independently hydrogen; aryl optionally containing one or more heteroatoms selected from the group consisting of N, S and O; lower acyloxy; phenyl; phenyl substituted with a halogen, lower alkyl group, lower acyl group or derivative thereof or acetamido; benzyl; benzyl substituted on the ring by one or more halogens, lower alkyl groups or both; cycloalkyl, which optionally contains one or more heteroatoms selected from the group consisting of N, O and S; lower alkyl; or lower alkyl substituted with an aromatic moiety. At least one of $R^3$ and $R^4$ is an aromatic ring or an aromatic ring containing moiety. As used herein, lower alkyl refers to a branched or straight chain alkyl group having eight or fewer carbons. Alkyl also includes hydrocarbon groups having one or two double or triple bonds in the chain. The present invention also includes salts of the aforementioned compounds. For new compounds and salts of the present invention, 1. when $R^1$ and/or $R^2$ is methoxymethyl, $R^3$ and $R^4$ are not both phenyl, are not both phenyl substituted by lower alkyl, and are not both phenyl substituted by halogen; and 2. when one of $R^3$ and $R^4$ is phenyl or benzyl, the other of $R^3$ and $R^4$ is not ethyl; and 3. when at least one of $R^1$ and $R^2$ is benzyl, then when one of $R^3$ and $R^4$ is phenyl, the other is not allyl; and 4. when one of $R^1$ and $R^2$ is methyl and the other is hydrogen, then when one of $R^3$ and $R^4$ is phenyl, the other of $R^3$ and $R^4$ is not unsubstituted lower alkyl; and 5. when $R^1=R^2=R^a$, where $R^a$ is alkoxymethyl or (acyloxy)methyl, then when one of $R^3$ and $R^4$ is 1-phenylethyl, the other of $R^3$ and $R^4$ is not propionyloxy.

Furthermore, the following compounds are not included within the scope of the present invention with respect to compositions, but can be used in practicing the method of the invention.

a) 1-methyl-5-(1-phenylethyl)-5-propionyloxy-barbituric acid,

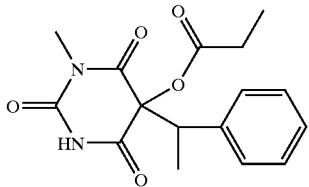

b) 1,3-diphenyl-5,5-(dibenzyl) barbituric acid,

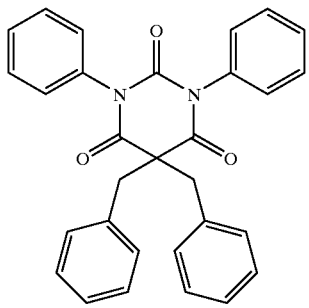

c) 1,3,5-triphenyl barbituric acid, and

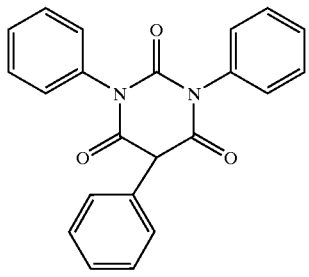

d) 5-benzyl-1,3-dimethyl barbituric acid.

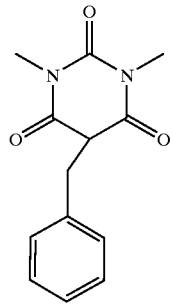

In some exemplary embodiments, at least one of $R^1$ and $R^2$ is lower alkyl substituted by lower cycloalkyl, acyl, acyloxy, aryl, aryloxy, thioalkyl or thioaryl, amino, alkylamino, dialkylamino, or one or more halogen atoms; phenyl; $CH_2SR^5$, wherein $R^5$ is lower alkyl, aryl, alkylaryl or benzyl; $C(S)XR^6$, wherein X is S or O and $R^6$ is lower alkyl or aryl; $CSR^7$, wherein $R^7$ is hydrogen, lower alkyl or aryl; and $CH(SR^8)_2$, wherein $R^8$ is a lower alkyl group.

In other exemplary embodiments, at least one of $R^3$ and $R^4$ is lower acyloxy; phenyl substituted with a lower acyl group or derivative thereof or acetamide; and cycloalkyl of which the ring optionally contains one or more heteroatoms selected from the group consisting of N, O and S.

In certain exemplary embodiments of the invention, the substituents $R^1$ and $R^2$ are different and are individually selected from butyl, benzyl, thiophenylmethyl, cyclopropylmethyl, 3,3,3-trifluoropropyl, benzyloxymethyl, and alkoxymethyl. In other exemplary embodiments, $R^1$ and $R^2$ are the same and are selected from butyl, benzyl, thiophenylmethyl, cyclopropylmethyl, 3,3,3-trifluoropropyl, benzyloxymethyl, and alkoxymethyl. In other exemplary embodiments, one of $R^1$ and $R^2$ is hydrogen and the other of $R^1$ and $R^2$ is selected from alkoxymethyl, butyl, benzyl, thiophenylmethyl, cyclopropylmethyl, 3,3,3-trifluoropropyl, and benzyloxymethyl. In other words, one of $R^1$ and $R^2$ is hydrogen, and the other of $R^1$ and $R^2$ is selected from:

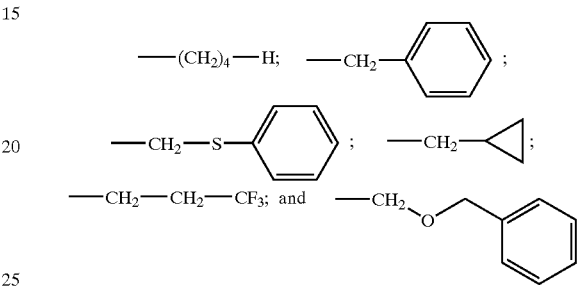

In other exemplary embodiments, at least one of $R^1$ and $R^2$ are methoxymethyl. In other exemplary embodiments, $R^3$ and $R^4$ are both aromatic rings or aromatic ring containing moieties.

In certain exemplary embodiments, $R^3$ and $R^4$ are the same or different and are independently phenyl; phenyl substituted with a halogen or lower alkyl group; cycloalkyl, which optionally comprises one or more heteroatoms selected from the group consisting of N, O and S; benzyl; benzyl substituted on the ring by one or more halogens, lower alkyl groups or both; lower alkyl; or lower alkyl substituted with an aromatic moiety, provided that at least one of $R^3$ and $R^4$ is phenyl or substituted phenyl.

In other exemplary embodiments, at least one of $R^3$ and $R^4$ are selected from the group consisting of phenyl, benzyl, fluorophenyl and tolyl.

In other exemplary embodiments, at least one of $R^3$ and $R^4$ is selected from:

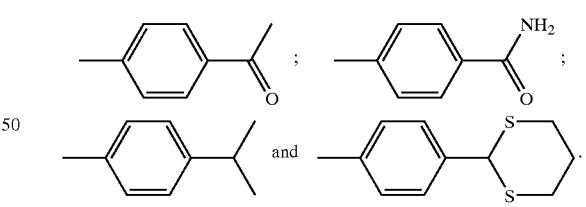

$R^3$ and $R^4$ may be the same or different.

$R^1$ and $R^2$ may function as non-toxic leaving groups capable of being removed in a biological system to give rise to a pharmacologically active species. The relatively slow loss of $R^1$ and/or $R^2$ results in an extension of the metabolic half-life of the pharmacologically active species in mammals. $R^3$ and $R^4$ may be chosen so that the resultant pharmacologically active compound avoids the sedative properties normally associated with barbituric acid derivatives. A modified version of the test described in Example 3 could serve as a test method for identifying compounds which do not have the sedative properties normally associated with barbituric acid derivatives. For example, if a test animal to which the compound has been administered fails to respond to a large fraction of imposed stimuli, the compound may be understood as having sedative properties. By testing a compound with particular $R^3$ and $R^4$ substituents, compounds not having the sedative properties normally associated with barbituric acid derivatives can be identified.

It has been reported (Rains A, Moros D et al., J. Exp. Biol. (Abstracts) 1996, 895; Epilepsia 1996, 37: Suppl. 5) that N,N'-dimethoxymethyl-5,5-diphenyl barbituric acid degrades metabolically to form diphenyl barbituric acid (DPB). It has also been learned that the degradation mechanism involves formation of the monomethoxymethyl intermediate. According to the invention, the N-substituted $R^1/R^2$ groups may be cleaved metabolically to produce the $R^3/R^4$ substituted compounds with mono or no N substitution or the $R^1/R^2$ groups may remain bound in an active compound.

Preferred compounds are those without adverse side effects. Examples of adverse side effects are toxicity, which can be assessed by the method of Example 2, and sedation, which can be assessed by the method of Example 3, as described above.

Placement of the 1 and 3 substituents to prepare 1,3-bis (substituted)-5,5-disubstituted barbituric acids according to the invention may be accomplished by reacting an appropriate 5,5-di(substituted) barbituric acid with an alkali hydride to form the corresponding barbiturate salt which is then reacted with a moiety having a leaving group in a process similar to that described by Samour et al. in J. Med. Chem. 14, 187 (1971). In a more general method, mono- and di-substituted compounds may be prepared according to the process described in U.S. Pat. No. 6,093,820 and modifications thereof. In general, a 5,5-disubstituted barbituric acid derivative is reacted with excess base. The dianion formed is then reacted with one equivalent of an alkylating agent if the monosubstituted derivative is desired, or two equivalents of alkylating agent, if the disubstituted derivative is desired.

Substituents at the 5-position may be prepared by reacting alloxan with an appropriate starting material in a manner similar to the preparation of diphenyl barbituric acid described by McElvain, referenced above. These substituents may also be placed on a 1,3-bis(substituted)-barbituric acid by oxidation of the acid to the corresponding 1,3-dialkyl alloxan, which is then reacted with an appropriate compound in a similar way to yield the desired product.

Compounds in their free acid form may be converted by techniques well known to persons of ordinary skill in the art into salts such as sodium, potassium or other pharmacologically acceptable salts.

The proper choice of synthetic method would be readily recognized by persons skilled in the art or readily derived through routine experimentation well known to persons of ordinary skill in the art of organic chemical synthesis. The novel compounds of the invention are not limited by their method of manufacture, but may be prepared by the methods described herein, other methods known to persons skilled in the art, or methods yet to be developed.

The term "treatment", as used herein, is intended to encompass administration of compounds according to the invention prophylactically to prevent or suppress an undesired condition, and therapeutically to eliminate or reduce the extent or symptoms of the condition. Treatment according to the invention is given to a human or other mammal having a disease or condition creating a need of such treatment. Treatment also includes application of the compound to cells or organs in vitro. Treatment may be by systemic or local administration.

The non-sedative barbituric acid derivatives of the present invention may be formulated into "pharmaceutical compositions" with appropriate pharmaceutically acceptable carriers, excipients or diluents. If appropriate, pharmaceutical compositions may be formulated into preparations including, but not limited to, solid, semi-solid, liquid, or gaseous forms, such as tablets, capsules, powders, granules, ointments, solutions, suppositories, injections, inhalants, and aerosols, in the usual ways for their respective route of administration.

An effective amount is the amount of active ingredient administered in a single dose or multiple doses necessary to achieve the desired pharmacological effect. A skilled practitioner can determine and optimize an effective dose for an individual patient or to treat an individual condition by routine experimentation and titration well known to the skilled clinician. The actual dose and schedule may vary depending on whether the compositions are administered in combination with other drugs, or depending on inter-individual differences in pharmacokinetics, drug disposition, and metabolism. Similarly, amounts may vary for in vitro applications. It is within the skill in the art to adjust the dose in accordance with the necessities of a particular situation without undue experimentation. Where disclosed herein, dose ranges do not preclude use of a higher or lower dose of a component, as might be warranted in a particular application.

Neurological disorders include strain and stress conditions and nervous dysfunctions such as convulsions, seizure, muscle stiffness, nervous strain and anxiety. The compounds of the present invention may be used as anticonvulsive agents and can therefore be employed in the treatment of epilepsy. The compounds of the present invention may also be used as neuroprotective agents for the treatment of cerebral ischemia, head trauma and other acute neurologic injuries, and in the prevention of resulting neuronal damage. The compounds may be used in individuals undergoing cardiac surgery or carotid endarterectomy, and individuals at risk for atrial fibrillation, transient ischemic attacks (TIAs), cerebral ischemia, bacterial endocarditis, strokes, or subarachnoid hemorrhage due to a cerebral aneurysm. The compounds can also be used after an acute event.

The useful doses of the non-sedative barbiturate useful for neuroprotective purposes may exceed the minimum anticonvulsant dosage of the barbiturate. In some embodiments of the present invention the useful dose of the non-sedative barbiturate is in the range of from about 2 times to about 5 times the anticonvulsant dosage. In yet other contexts where the need of the mammal requires, the effective dose of the non-sedative barbiturate for neuroprotective purposes is in the range of from about 5 times to about 10 times the anticonvulsant dosage of the non-sedative, or even higher so long as the dose is clinically acceptable. In particular, the useful doses may exceed the dose of a sedative barbiturate, such as Phenobarbital, at which sedation occurs and may exceed the doses at which coma or death would occur for Phenobarbital.

The neuroprotective effect of the present methods can be used to mitigate the effect of cerebral ischemia. The non-sedating barbiturate can be administered orally, intravenously, transdermally, in combination with an adjuvant, or transpulmonarily by means of a particulate or aerosol inhalant. Moreover, within the scope of the invention, the non-sedating barbiturate can be administered preventively, prophylactically or therapeutically, at a clinically acceptable dose. The compound may be administered prophylactically before evident neuronal damage, or therapeutically after onset of neuronal damage. The neuroprotective effect diminishes, or protects the subject from neuronal damage caused by head trauma or cerebral ischemia. The compound may be administered in conjunction with cardiac surgery or carotid endarterectomy. The mammalian subject may have or be at risk for atrial fibrillation, a transient ischemic attack (TIA), bacterial endocarditis, a stroke, head trauma, or subarachnoid hemorrhage.

Typically, to achieve neuroprotection the non-sedating barbiturate is administered in a dose sufficient to obtain blood concentrations of at least about 30 $\mu$g/ml of barbiturate or of an active metabolite thereof, preferably at least about 100 $\mu$g/ml, more preferably at least about 250 $\mu$g/ml, and possibly as high as 200–300 $\mu$g/ml, or even higher. In contrast, the reported therapeutic range for phenobarbital is lower, 10–30 $\mu$g/ml blood levels. Thus, preferred ranges are at or above about 25, 30, 50, 75, 100, 200, 250, or 300 $\mu$g/ml. Similar doses are suitable for the other pharmaceutical effects described herein.

The invention includes a pharmaceutical composition comprising a non-sedating barbiturate administered in an amount effective to have a neurological effect. Preferably, the non-sedating barbiturate is administered in oral doses in the range of from about 25 to about 1,500 mg/kg/day body weight. Preferably the dose is greater than about 50 mg/kg/day, or greater than about 100 mg/kg/day, or greater than 250 mg/kg/day. A preferred dose is one that is pharmacologically equivalent to a dose of about 1000 mg/kg/day in the rat. Thus, dosage forms may be sufficient individually or in multiple doses to provide a dose equal to or above about 1, 5, 10, 15, 20, 25, 50, 70, 100, 250, 500, 1000, or 1500 mg/kg body weight per day. For other therapeutic uses, lower doses are suitable in the range of over or about 0.1, 0.5, 1, 5, or 10 mg/kg body weight per day and other doses as are well known in respect to barbiturates.

The inventive barbituric acid derivatives have prolonged half-life in humans making it possible to achieve substantial blood levels with lower oral dosages. Blood levels of non-sedating barbiturates greater than 100 $\mu$g/ml may be achieved with, for example, dosages between about 40 and about 100 mg/kg/day, and are within the scope of the invention. With parenteral administration of non-sedating barbiturates, similar blood concentrations are obtained with daily dosages of less than 25 mg/kg/day. However, first day loading dosages may still need initial dosages of greater than 25 mg/kg.

It is generally believed that the neurological, e.g. anticonvulsant and neuroprotective, effects of barbiturates are linked to their sedative/hypnotic effects. For example, Lightfoote et al. in Stroke 8, 627–628 (1977) suggested that the protective effects of pentobarbital are due to the duration of the barbiturate-induced anesthesia. This viewpoint has been reinforced by biochemical studies at the cell receptor level that relate all these effects to action at the GABA receptor. Thus, the prior art teaches away from using sedative barbiturates for neuroprotection because of their toxicity, and also teaches away from using non-sedative barbiturates as neuroprotectants because they lack sedating or anesthetic properties.

The invention also provides for pharmaceutical compositions comprising as active material a compound of the above general Formula I or a pharmaceutically acceptable salt thereof together with one or more pharmaceutically acceptable carriers, excipients or diluents. Any conventional technique may be used for the preparation of pharmaceutical formulations according to the invention. The active ingredient may be contained in a formulation that provides quick release, sustained release or delayed release after administration to the patient.

Pharmaceutical compositions that are useful in the methods of the invention may be prepared, packaged, or sold in formulations suitable for oral, parenteral and topical administration. Other contemplated formulations include nanoparticles, liposomal preparations, resealed erythrocytes containing the active ingredient, and immunologically-based formulations.

The formulations of the pharmaceutical compositions described herein may be prepared by any method known or hereafter developed. In general, preparation includes bringing the active ingredient into association with a carrier or one or more other additional components, and then, if necessary or desirable, shaping or packaging the product into a desired single- or multi-dose unit.

Prolonged activity is a valuable attribute of drugs in general and of anticonvulsant drugs in particular. Aside from allowing infrequent administration, it also improves patients' compliance with the drug. Furthermore, serum and tissue levels, which are crucial for maintaining therapeutic effectiveness, are more stable with a long acting compound. Moreover, stable serum levels reduce the incidence of break-through seizures and possible other adverse effects.

As used herein, "additional components" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; pharmaceutically acceptable polymeric or hydrophobic materials as well as other components.

Although the descriptions of pharmaceutical compositions provided herein are principally directed to pharmaceutical compositions which are suitable for administration to humans, it will be understood by the skilled artisan, based on this disclosure, that such compositions are generally suitable for administration to any mammal. Preparation of compositions suitable for administration to various animals is well understood, and the ordinarily skilled veterinary pharmacologist can design and perform such modifications with routine experimentation based on pharmaceutical compositions for administration to humans.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient in each unit dose is generally equal to the total amount of the active ingredient which would be administered or a convenient fraction of a total dosage amount such as, for example, one-half or one-third of such a dosage.

A formulation of a pharmaceutical composition of the invention suitable for oral administration may be in the form of a discrete solid dosage unit. Solid dosage units include, for example, a tablet, a caplet, a hard or soft capsule, a cachet, a troche, or a lozenge. Each solid dosage unit contains a predetermined amount of the active ingredient, for example a unit dose or fraction thereof. Other formulations suitable for administration include, but are not limited to, a powdered or granular formulation, an aqueous or oily suspension, an aqueous or oily solution, or an emulsion. As used herein, an "oily" liquid is one which comprises a carbon or silicon based liquid that is less polar than water.

A tablet comprising the active ingredient may be made, for example, by compressing or molding the active ingredient, optionally containing one or more additional components. Compressed tablets may be prepared by compressing, in a suitable device, the active ingredient in a free-flowing form such as a powder or granular preparation, optionally mixed with one or more of a binder, a lubricant, a glidant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Tablets may be non-coated or they may be coated using methods known in the art or methods to be developed. Coated tablets may be formulated for delayed disintegration in the gastrointestinal tract of a subject, for example, by use of an enteric coating, thereby providing sustained release and absorption of the active ingredient. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional components including, for example, an inert solid diluent. Soft gelatin capsules comprising the active ingredient may be made using a physiologically degradable composition, such as gelatin. Such soft capsules comprise the active ingredient, which may be mixed with water or an oil medium.

Liquid formulations of a pharmaceutical composition of the invention which are suitable for administration may be prepared, packaged, and sold either in liquid form or in the form of a dry product intended for reconstitution with water or another suitable vehicle prior to use.

Liquid suspensions, in which the active ingredient is dispersed in an aqueous or oily vehicle, and liquid solutions, in which the active ingredient is dissolved in an aqueous or oily vehicle, may be prepared using conventional methods or methods to be developed. Liquid suspension of the active ingredient may be in an aqueous or oily vehicle and may further include one or more additional components such as, for example, suspending agents, dispersing or wetting agents, emulsifying agents, demulcents, preservatives, buffers, salts, flavorings, coloring agents, and sweetening agents. Oily suspensions may further comprise a thickening agent. Liquid solutions of the active ingredient may be in an aqueous or oily vehicle and may further include one or more additional components such as, for example, preservatives, buffers, salts, flavorings, coloring agents, and sweetening agents.

Powdered and granular formulations according to the invention may be prepared using known methods or methods to be developed. Such formulations may be administered directly to a subject, or used, for example, to form tablets, to fill capsules, or to prepare an aqueous or oily suspension or solution by addition of an aqueous or oily vehicle thereto. Powdered or granular formulations may further comprise one or more of a dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. Such compositions may further comprise one or more emulsifying agents. These emulsions may also contain additional components including, for example, sweetening or flavoring agents.

The efficacy of the compounds of the invention with respect to strain and stress conditions and nervous dysfunctions such as convulsions, seizure, muscle stiffness, nervous strain and anxiety may be tested as set forth in non-limiting examples 1–3 below. Similarly, the neuroprotective ability of the compounds may be tested as set forth by, for example, the general method described in non-limiting example 4 with specific reference to non-limiting examples 5–7. Other methods known or to be developed may similarly be used to test the compounds of the invention.

Compounds according to the invention can be made by two general synthetic routes, using methods generally known in the art, or modifications thereof that are known or readily derived by persons of ordinary skill in the art without undue experimentation. Exemplary methods for various steps can be found in, for example, Loudon, G. M., *Organic Chemistry*, Addison-Wesley, 1984; U.S. Pat. No. 4,628,056 to Levitt et al. (1986); U.S. Pat. No. 6,093,820 to Gutman et al. (2000); published European Patent Application No. 1 083 172 A1 to Ashkinazi (2001); and U.S. Pat. No. 5,750,766 to Krummel et al. (1998), each of which is incorporated herein by reference in its entirety. Scheme 1 is a retrosynthetic analysis outlining routes to the inventive compounds.

Compounds of Formula I can be prepared by N-alkylation of an appropriately substituted barbituric acid derivative (Formula II). Suitable exemplary methods for N-alkylation of barbituric acids are given below in Examples 8a, 8b, 9a, 9b, 10, 11, and 12. Other known methods will be known to persons skilled in the art and may also be used. The required barbituric acid derivatives of Formula II can be prepared by condensation of urea with a suitable substituted malonic ester (Formula III). In an alternative synthetic route (See Example 8c), the barbituric acid derivatives of Formula I can be prepared by reacting a substituted urea (Formula IV) with a suitably substituted malonic ester (III). Preparation of substituted ureas is well known. Methods of preparing compounds of Formula III are also known in the art. Suitable exemplary methods of their preparation, in which $R^3$ and/or $R^4$ may substituted, are given in Examples 13–16. Other methods will be known to persons skilled in the art and may also be used.

Scheme I

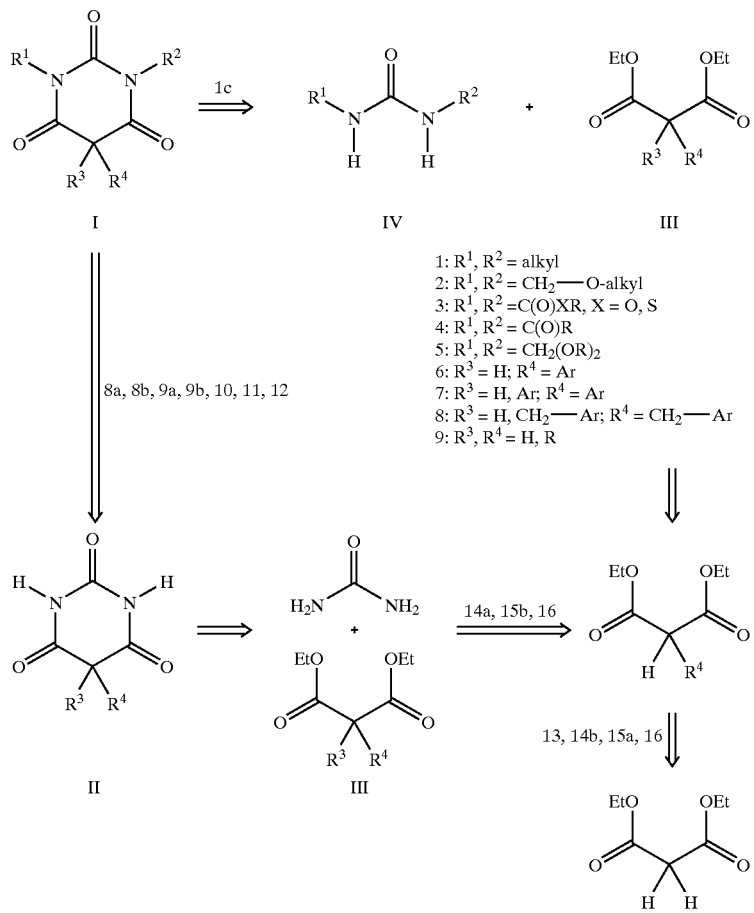

1: $R^1, R^2$ = alkyl
2: $R^1, R^2$ = $CH_2$—O-alkyl
3: $R^1, R^2$ =C(O)XR, X = O, S
4: $R^1, R^2$ = C(O)R
5: $R^1, R^2$ = $CH_2(OR)_2$
6: $R^3$ = H; $R^4$ = Ar
7: $R^3$ = H, Ar; $R^4$ = Ar
8: $R^3$ = H, $CH_2$—Ar; $R^4$ = $CH_2$—Ar
9: $R^3, R^4$ = H, R

EXAMPLE 1

The anticonvulsant activity of the barbituric acid derivatives of the invention may be demonstrated or tested by evaluating the protection against a maximal electro shock seizure (MES) in treated rats. MES tests are widely used for the assessment of anticonvulsant properties of chemical compounds, mainly due to the good correlation between the test results and the clinical finding of efficacy in patients suffering from epilepsy. In a typical MES test carried out to evaluate the anticonvulsant properties of barbituric acid derivatives of the invention, corneal electrodes are employed, a current of about 150 milliamperes is used and a 60 hertz stimulus applied for about 200 milliseconds. Rats are tested on the day prior to drug administration so as to eliminate from the study any animals failing to respond with a complete tonic convulsion including tonic hind-limb extension (THE), which serves as the basis for the assessment of the efficacy of the active material employed. Animals protected from THE are regarded as protected in the MES tests.

The test composition is dissolved in warm polyethylene glycol 400 or other suitable solvent and the solution administered in an initial dose of about 500 mg/kg by stomach tube to, for example, Sprague-Dawley rats. These animals are tested for maximum electro shock seizure (MES) at a predetermined time after administration, for example, about 6 and 23 hours after administration. All animals are demonstrated to exhibit a full maximal seizure to electrical stimulation prior to being accepted for the study.

EXAMPLE 2

The non-toxicity of barbituric acid derivatives of the invention can be tested by repeated administration of a high dosage, as follows:

The test compound suspended in warm polyethylene glycol 400 or other suitable solvent is administered in an initial dose of about 1500 mg/kg by gastric tube to, for example, Sprague Dawley rats. A similar dose is administered to same rats after 24 hours and again 48 hours after the first administration. Animals are examined for several hours after administration, again prior to the next dosing, and through an additional 3 days after the last administration. The toxic effects of administration are monitored as well as behavioral effects such as, for example, locomotion, escape behavior, feeding or any other observable effect.

EXAMPLE 3

The tranquilizing and muscle relaxant properties of the barbituric acid derivatives of the invention can be demonstrated by monitoring the behavioral and motor effects observed with treated mice.

For example, the test composition in alkalinized saline may be administered intraperitoneally to, for example, Swiss Webster mice. The time required for animals receiving various doses to exhibit particular motor and behavioral effects is noted. Effects monitored may include, for example, muscle hypotonia, motor activity, quietness and escape behavior. Toxic effects are also noted.

The efficacy of the composition can be evaluated relative to known centrally acting skeletal muscle relaxants and/or tranquilizing drugs. The combination of the tranquilizing effect without impairing the capacity of the animal to react to its environment is highly desirable in agents used for the treatment of anxiety. Hypnotic activity or depression of the central nervous system is preferably not exhibited by the compositions of the invention.

EXAMPLE 4

General Design for Determining Efficacy for Treatment of Ischemia

The non-sedative barbituric acid derivatives of the invention (NSB) may be tested in rats exposed to either reversible or irreversible ischemia. Varying doses of drug are administered. The neuroprotective effect is compared to a negative control (placebo) and a positive control, pentobarbital, a known neuroprotective but sedative barbiturate, given at doses known to reduce infarct volume in cerebral ischemia.

Animals are sacrificed several days after the onset of the ischemic insult and the brains examined to determine the volume of brain infarction as an outcome measure of the drug's reduction of ischemic brain damage. The animals are examined clinically and graded prior to sacrifice to determine if the drug has conferred any beneficial effect on relevant functions following ischemic "stroke."

Four experimental models are preferred for testing the neuroprotective effects of the NSB drug. See Ginsberg M D, "Animal Models of Global and Focal Cerebral Ischemia," Chapter 34 in Welsh K M A et al., *Primer on Cerebrovascular Diseases*, Academic Press, New York, 1997; and Pulsinelli W A, Brierley J B, A new model of bilateral hemispheric ischemia in the unanesthetized rat, Stroke 1979, May–Jun. 10(3):267–72. These references are hereby incorporated by reference.

1. Irreversible ischemia produced by middle cerebral artery (MCA) occlusion;
2. Reversible ischemia produced by MCA occlusion;
3. Transient global ischemia produced by cross-clamping the aorta for a defined interval; and
4. Transient global ischemia produced by cauterizing both vertebral arteries and reversibly clamping the common carotid arteries.

In each experimental model, groups of rats are treated with either:

1. Negative control (placebo) via nasogastric (NG) tube;
2. Positive control: intraperitoneal (IP) dose of 70 mg/kg pentobarbital; or
3. The NSB compound DMMDPB (or a compound being tested for its utility in the present invention) via NG tube at doses between 500 mg/kg and 1500 mg/kg for 7 days prior to experimental infarctions.

The results are compared.

EXAMPLE 5

Irreversible Cerebral Ischemia

Irreversible MCA occlusion is produced by ligating the carotid artery and then inserting a filament into the origin of the MCA with the animal maintained under halothane anesthesia. Blood flow in the MCA is measured by laser doppler and those animals in which a significant drop in blood flow occurred are considered to have experienced cerebral ischemia, and to be at risk for subsequent damage (i.e., a stroke). No clinical strokes are expected in animals that do not experience a precipitous drop in MCA blood flow. All animals showing a drop in MCA blood flow are expected to experience strokes.

Animals at risk are then followed behaviorally and scored by clinical findings using the Bederson grading scale as either:

0 no evidence of stroke
1 mild stroke
2 moderate stroke
3 severe stroke

Those animals that survive for three days are sacrificed and their brains examined. Animals to be sacrificed are given, for example, chloral hydrate (35 mg/kg IP, and their brains fixed by intracardiac perfusion with heparinized 0.9% saline followed by 10% buffered formalin. The brains are removed from the cranial vault with care to leave the arachnoid intact with the intracranial vessels underneath. The fixed brains are frozen at. for example, 80° C. Coronal sections 20 $\mu$m thick are cut at 400 $\mu$m intervals in a cryostat at –20° C., dried on a hot plate at 60° C., fixed in 90% ethanol for 10 minutes and stained with hematoxylin and eosin (7). Infarcted brain is pale compared to the rest of the brain. The amount of infarcted brain is determined by microscopic inspection of the brain sections and calculation of infarct volumes in mm$^3$.

EXAMPLE 6

Reversible Cerebral Ischemia Model

Rats are pretreated as in Example 4 (above) and a similar procedure is performed except that the filament occluding the MCA is removed after 30 to 60 minutes, restoring blood flow through the MCA. Rats are then followed clinically for three days, graded for their degree of stroke and then sacrificed as in Example 5. The brains are removed and examined as described above.

EXAMPLE 7

Rats are pretreated as in Example 4 (above) and then, during ether anesthesia, the rats' vertebral arteries are electrocauterized through the alar foramina of the first cervical vertebra. Reversible clamps are then placed loosely around the common carotid arteries. After 24 hours, working with awake rats, the carotid clamps are tightened to produce 4-vessel occlusion. Following 10–30 minutes of 4-vessel occlusion, the clamps are removed and 72 hours later the animals sacrificed by perfusion fixation. Untreated rats routinely demonstrate ischemic neuronal damage after 20 or 30 minutes of 4-vessel occlusion. Multiple areas of the forebrain, including the H1 and paramedian hippocampus, striatum, and posterior neocortex are evaluated. The NSBs are shown to be neuroprotective under these circumstances.

EXAMPLE 8a

Preparation of Mono and Bis N-Alkylated Barbituric Acids

A compound of Formula II is dissolved with potassium hydroxide in ethanol. An alkyl halide, R'X, is dissolved in the solution; the solutes react. The product of Formula I with $R^1=R^2=R'$. (Loudon G M, *Organic Chemistry*, Addison-Wesley (1984), p. 1194)

EXAMPLE 8b

Preparation of Mono and Bis N-Alkylated Barbituric Acids

A compound of Formula II is dissolved with potassium hydroxide in ethanol. An alkyl tosylate, R'O Ts, is dissolved in the solution; the solutes react. The product has Formula I with $R^1=R^2=R'$. (Loudon G M, *Organic Chemistry*, Addison-Wesley (1984), p. 1194)

EXAMPLE 8c

Preparation of Mono and Bis N-Alkylated Barbituric Acids by Condensation of a Urea and a Malonic Ester A urea substituted with an alkyl group at one or both amides is used as a starting material (Formula IV). If disubstituted, the alkyl grouping may be the same or different, i.e., the first alkyl group may be R', and the second alkyl group may be R' or R", where R' and R" are different. The substituted urea is then reacted with a malonic ester (Formula III), e.g., diethyl malonate, and sodium ethoxide in ethanol. The reaction product has Formula I with $R^1=R'$ and $R^2=H$, R' or R". (Loudon G M, *Organic Chemistry*, Addison-Wesley (1984), p. 1087; Euro. Pat. Applic. No. 1 083 172 A1)

A range of alkyl groups having cycloalkyl, acyl, acyloxy, aryl, aryloxy, alkoxy, alkylthio, arylthio, amino, alkylamino, dialkylamino, or halogen groups can be substituted for $R^1$ and $R^2$ of Formula I using methods similar to those described in Examples 8a, 8b, and 8c.

EXAMPLE 9a

Preparation of N-Alkoxyalkylated Compounds

Dialkoxymethane (R'OCH$_2$OR') is added at 0° C. to acetylmethanesulfonate. The temperature of the solution is raised to 25° C. and the components allowed to react for 2 hours. The resultant solution is then added gradually over 45 minutes to a mixture of a suitably substituted barbituric acid (Formula II) and sodium hydride (as a 60% dispersion in mineral oil) in dry dimethylformamide. The resultant reaction mixture is stirred for about 15 minutes and then diluted with hydrochloric acid, followed by dilution with ethyl acetate. The phases are separated and the ethyl acetate phase washed with a saturated aqueous sodium chloride and then washed with aqueous sodium hydroxide. The ethyl acetate phase is then dried over anhydrous sodium sulfate, filtered, and concentrated to dryness. The dried product is then crystallized from toluene and has the structure of Formula I with $R^1=R^2=CH_2OR$. (U.S. Pat. No. 6,093,820)

By using different barbituric acid derivatives as starting materials, the $R^3$ and $R^4$ groups may be varied.

By using an excess of sodium hydride and one equivalent of alkylating agent, monosubstitution is favored, such that most of the product consists of material of Formula I with one of $R^1$ and $R^2$ being substituted as $CH_2OR'$ and the other being substituted with hydrogen.

EXAMPLE 9b

Alternative Preparation of N-Alkoxyalkylated Compounds

A suitable barbituric acid (Formula II) is dissolved in dimethylformamide. Once the solution has cooled, sodium hydride is added and the mixture stirred for 30 minutes. An appropriate chloromethyl alkyl ether is added to the mixture over a period of about 30 minutes. The reaction mixture is then stirred for 1 hour, then poured into ice water. The solid precipitate is filtered, washed with water, and crystallized from ethanol. (U.S. Pat. No. 4,628,056)

By using different barbituric acid derivatives as starting materials, the $R^3$ and $R^4$ groups may be varied.

Different alkoxides can be substituted as $R^1$ and $R^2$ by using different chlorinated ethers. For example, groups of $R^1=R^2=CH_2OR'$ can be formed wherein R' is alkyl, aryl, alkylaryl, or benzyl. Alkylthio groups can be substituted as $R^1$ and $R^2$ by using chlorinated thioethers. For example, groups of $R^1=R^2=CH_2SR'$ can be formed wherein R' is alkyl, aryl, alkylaryl, or benzyl.

EXAMPLE 10

Preparation of N-Acyloxy Substituted Barbituric Acids

A compound of Formula II is dissolved with an alkyl chloroformate in a solution containing sodium hydroxide. The product of the reaction has Formula I with $R^1=R^2=C(O)OR'$, wherein R' is alkyl.

By reacting a compound of Formula II with an aryl chloroformate in a solution containing sodium hydroxide, a product is formed which has Formula I with $R^1=R^2=C(O)OR'$, wherein R' is aryl. (Loudon, pp. 1061–1064)

By reacting a compound of Formula I with a compound of the formula, ClC(O)SR', wherein R' is alkyl or aryl, a product is formed which has Formula I with $R^1=R^2=C(O)SR'$, wherein R' is alkyl or aryl.

EXAMPLE 11

Preparation of N-Acyl Substituted Barbituric Acids

A compound of Formula II is dissolved with an acid chloride of the formula ClC(O)R', where R' is hydrogen, alkyl, or aryl and allowed to react over an aqueous solution of sodium hydroxide. The product has Formula I, wherein $R^1=R^2=C(O)R'$. (Loudon G M, *Organic Chemistry*, Addison-Wesley (1984), pp. 1062–1064)

EXAMPLE 12a

Preparation of N-Acetal Substituted Barbituric Acids

A compound having Formula II is dissolved in dimethylformamide. Sodium hydride is added to the solution. A chlorinated diether having the general formula, ClCH(OR')$_2$, wherein R' is alkyl, is added to the solution. The reactant product is then purified. The product has Formula I with $R^1=R^2=CH(OR')_2$. (Loudon G M, *Organic Chemistry*, Addison-Wesley (1984), pp. 1062–1064)

EXAMPLE 12b

Preparation of N-Arylmethyl Substituted Barbituric Acid

A compound of Formula II is dissolved with potassium hydroxide in ethanol. A halomethyl substituted aromatic compound, ArCH$_2$X, wherein X is halogen, is dissolved in the solution. The reaction product has Formula I with $R^1=R^2=CH_2Ar$. (Loudon G M, *Organic Chemistry*, Addison-Wesley (1984), p. 1194)

This synthesis method can also be conducted with benzyl chloride substituted on the benzene ring with sulfur hydride, SH.

EXAMPLE 12c

Preparation of N-Thioaryl Substituted Barbituric Acid

A compound of Formula II is dissolved with potassium hydroxide in ethanol. A thiohaloarylalkyl compound, R'ArSX, wherein X is halogen and R' is H or alkyl, is dissolved in the solution. The reaction product has Formula I with $R^1=R^2=SArR'$.

EXAMPLE 13

Preparation of 5-Aryl Substituted Barbituric Acid Derivatives

A solution of magnesium in an inert solvent is made. The inert solvent can be selected from the group consisting of diethylether, dimethoxymethane, tert-butylmethylether, tetrahydropyran, diisopropylether, toluene, and mesitylene and can be a mixture of these solvents. Including either 1,2-dibromomethane or diethylether can be beneficial. In a first step, an arylmethylhalide is added to the solution. The aryl group may be a heteroaromatic group containing nitrogen in the ring and optionally containing carbon, oxygen, or sulfur in the ring. The solution can also contain tri-n-butylamine.

Diethylcarbonate is then added to the solution followed by neutralization with hydrochloric acid. The organic layer is then separated.

Sodium ethylate is added to the concentrated organic layer. Ethanol is then distilled from the solution. The solution is neutralized with hydrochloric acid. The organic layer is then separated, dried, and concentrated in vacuum to yield a diethyl arylmalonate.

The diethyl arylmalonate is then dissolved with urea and sodium ethoxide in ethanol. The reaction product has Formula I with one of $R^3$ and $R^4$ being aryl, and the other of $R^3$ and $R^4$ being hydrogen. (U.S. Pat. No. 5,750,766; Loudon G M, *Organic Chemistry*, Addison-Wesley (1984), p. 1087)

EXAMPLE 14a

Preparation of 5-Aryl Substituted Barbituric Acid Derivatives

Alloxan monohydrate (Formula I, with $R^3=R^4=OH$) is dissolved in sulfuric acid. An aromatic compound (Ar—H) is added and the solution is heated and time allowed for the reaction to occur. The reaction mixture is then cooled, and the sulfuric acid layer is separated. The sulfuric acid layer is poured into cold water to precipitate the product. The precipitated product is filtered, washed, and refiltered, dried, an, if necessary, chromatographed to obtain the pure product of Formula I with $R^3=R^4=Ar$. (U.S. Pat. No. 4,628,056)

Using this method, a halogen-substituted benzene, e.g., fluorobenzene, can be used to obtain product of Formula I with $R^3=R^4=PhX$, wherein X is halogen. (U.S. Pat. No. 4,628,056)

Alternatively, an alkyl-substituted benzene, e.g., ethylbenzene, can be used to obtain product of Formula I with $R^3=R^4=PhR'$, wherein R' is alkyl. (U.S. Pat. No. 4,628,056)

In another variation, an acyl-substituted benzene can be used to obtain product of Formula I with $R^3=R^4=PhC(O)R'$, wherein R' is alkyl; or, benzylformamide can be used to obtain a product of Formula I with $R^3=R^4=PhCH_2C(O)NH_2$ or a dithiane-substituted benzene, having the structure

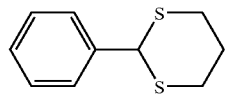

can be used to obtain a product of Formula I with $R^3=R^4=$Ph-dithiane.

EXAMPLE 14b

Preparation of 5-Aryl Substituted Barbituric Acid Derivatives

A solution of magnesium, dimethoxymethane, and dibromomethane is made. A halomethyl substituted aromatic compound in dimethoxymethane is added and allowed to react. Cold diethoxycarbonate is added to the solution. The solution is then neutralized with hydrochloric acid. The organic layer is separated and concentrated by distillation.

Sodium ethylate is added to the concentrated organic layer. Dimethoxymethane and ethanol are distilled from the solution. The solution is neutralized with hydrochloric acid and the organic layer separated, dried with magnesium sulfate, and concentrated in vacuum. The resultant product is an aromatic substituted diethyl malonate.

The diethyl malonate is then dissolved with urea and sodium ethoxide in ethanol and reacts. The reaction product has Formula I with one of $R^3$ and $R^4$ being aromatic and the other of $R^3$ and $R^4$ being hydrogen. (U.S. Pat. No. 5,750, 766; Loudon G M, *Organic Chemistry*, Addison-Wesley (1984), p. 1087)

Persons of ordinary skill in the art can use this method or variants thereof to synthesize barbituric acid derivatives from halomethyl substituted aromatic compounds which have additional substituents on the ring, e.g., halogen, alkyl, acyl, acyl derivative, or acetamido substituents on the ring, in order to obtain a product having Formula I with one of $R^3$ and $R^4$ being substituted aromatic and the other of $R^3$ and $R^4$ being hydrogen.

This synthesis method can also be conducted with chloromethylphenyl dithiane as the halomethyl substituted aromatic compound.

EXAMPLE 15a

Preparation of 5-Arylmethyl Substituted Barbituric Acid Derivatives

Diethyl malonate is dissolved with a bromomethyl substituted aromatic compound, having formula $ArCH_2X$, where Ar is aryl and X is halogen, and sodium ethoxide in ethanol. The product is a mono-arylmethylmalonate ester of formula $ArCH_2CH(CO_2Et)_2$. The monoarylmethylmalonate ester is then dissolved with urea and sodium ethoxide in ethanol and reacts. The reaction product has Formula I with $R^1=R^2=H$, with one of $R^3$ and $R^4$ being $CH_2Ar$, and the other of $R^3$ and $R^4$ being hydrogen. (Loudon G M, *Organic Chemistry*, Addison-Wesley (1984), pp. 617, 1086–1088)

The aromatic compound can be further substituted in the ring with, e.g., a halogen or an alkyl group.

EXAMPLE 15b

Preparation of 5,5-Bis(arylmethyl) Substituted Barbituric Acid Derivatives

Diethyl malonate is dissolved with a bromomethyl substituted aromatic compound, having formula $ArCH_2X$, where Ar is aryl and X is halogen, and sodium ethoxide in ethanol. The product is a mono-arylmethylmalonate ester of formula ArCH$_2$CH(CO$_2$Et)$_2$. The mono-arylmethylmalonate ester is separated from the solution. The separated mono-arlymethylmalonate ester is then dissolved with an iodomethyl substituted aromatic compound, having formula Ar'CH$_2$I, where Ar' is aryl and Ar and Ar' may be the same or different, and sodium ethoxide in ethanol. The product is a diarylmethyl-malonate ester of formula (ArCH$_2$)(Ar'CH$_2$)C(CO$_2$Et)$_2$.

The di-arylmethylmalonate ester is then dissolved with urea and sodium ethoxide in ethanol. The reaction product has Formula I with R$^3$=CH$_2$Ar; R$^4$=CH$_2$Ar'. (Loudon G M, *Organic Chemistry*, Addison-Wesley (1984), pp. 617, 1086–1088)

The aromatic ring of either compound can be substituted with, e.g., a halogen or an alkyl group.

EXAMPLE 16a

Preparation of 5,5-Dialkyl Substituted Barbituric Acid Derivatives

A compound having Formula I with R$^3$=R$^4$=OH is dissolved with tosyl chloride in pyridine to replace the hydroxy groups with tosyl groups. The resultant tosylate is isolated and redissolved with a lithium dialkylcuprate having the formula R'$_2$Cu$^-$Li$^+$, wherein R'=alkyl, in ether. The product has Formula I with R$^3$=R$^4$=R'. (Loudon G M, *Organic Chemistry*, Addison-Wesley (1984), pp. 721–722)

EXAMPLE 16b

Preparation of 5-Alkyl Substituted Barbituric Acid Derivatives

Diethyl malonate is dissolved with an alkyl bromide, having formula R'Br, wherein R' is alkyl, and sodium ethoxide in ethanol. The product is a mono-alkylmalonate ester of formula R'CH(CO$_2$Et)$_2$. The mono-alkylmalonate ester is then dissolved with urea and sodium ethoxide in ethanol and reacts. The reaction product has Formula I with one of R$^3$ and R$^4$ being R', and the other of R$^3$ and R$^4$ being hydrogen. (Loudon G M, *Organic Chemistry*, Addison-Wesley (1984), pp. 1086–1088)

The alkyl, R', may be substituted; e.g., the alkyl, R', may be substituted with an aromatic group.

EXAMPLE 16c

Preparation of 5,5-Dialkyl Substituted Barbituric Acid Derivatives

Diethyl malonate is dissolved with an alkyl bromide, having formula R'Br, wherein R' is alkyl, and sodium ethoxide in ethanol. The product is a mono-alkylmalonate ester of general formula R'CH(CO$_2$Et)$_2$. The mono-alkylmalonate ester is separated from the solution. The separated mono-alkylmalonate ester is then dissolved with an alkyl iodide, having formula R"I, wherein R" is alkyl and may be the same as or different from R', and sodium ethoxide in ethanol. The product is a di-alkylmalonate ester of formula R"R'C(CO$_2$Et)$_2$.

The di-alkylmalonate ester is then dissolved with urea and sodium ethoxide in ethanol. The reaction product has Formula II with one of R$^3$ and R$^4$ being R', and the other of R$^3$ and R$^4$ being R". R' and R" may be the same or different alkyls. (Loudon G M, *Organic Chemistry*, Addison-Wesley (1984), pp. 1086–1088)

The alkyls, R' and R", may be substituted; e.g., the R' and R" alkyls may each be substituted with an aromatic group.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A pharmaceutical composition, comprising as active material a non-sedative barbiturate, together with a pharmaceutically acceptable carrier, the composition being non-sedative and non-hypnotic when administered at a dose which is neuroprotective, the barbiturate having the structure

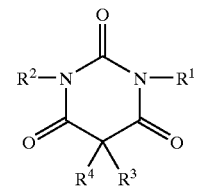

wherein
R$^1$ and R$^2$ may be the same or different and are independently lower alkyl, substituted by lower cycloalkyl, acyl, acyloxy, aryl, aryloxy, thioalkyl or thioaryl, amino, alkylamino, dialkylamino, or one or more halogen atoms;
phenyl;
C(O)XR$^6$, wherein X is S or O and R$^6$ is lower alkyl or aryl;
CXR$^7$, wherein X is as defined above and R$^7$ is hydrogen, lower alkyl or aryl; and
CH(XR$^8$)$_2$, wherein X is as defined above and R$^8$ is a lower alkyl group, with the proviso that at least one of R$^1$ and R$^2$ is not hydrogen; and wherein R$^3$ and R$^4$ may be the same or different and are independently hydrogen;
aryl optionally containing one or more heteroatoms selected from the group consisting of N, S, and O;
lower acyloxy;
phenyl substituted with lower acyl group or derivative thereof or acetamide;
benzyl; benzyl substituted on the ring by one or more halogens, lower alkyl groups or both; cycloalkyl, which optionally contains one or more heteroatoms selected from the group consisting of N, O, and S;
lower alkyl; or lower alkyl substituted with an aromatic moiety; provided that at least one of R$^3$ and R$^4$ is an aromatic ring or an aromatic ring containing moiety, and salts thereof, with the proviso that:
when one of R$^3$ and R$^4$ is benzyl, the other of R$^3$ and R$^4$ is not ethyl;
the compound is other than
a) 1-methyl-5-(1-phenylethyl)-5-propionyloxy-barbituric acid,
b) 1,3-diphenyl-5,5-(dibenzyl) barbituric acid,
c) 1,3,5-triphenyl barbituric acid, and
d) 5-benzyl-1,3-dimethyl barbituric acid.

2. A pharmaceutical composition, comprising as active material a non-sedative barbiturate, together with a pharmaceutically acceptable carrier, the composition being non-sedative and non-hypnotic when administered at a dose which is neuroprotective, the barbiturate having the structure

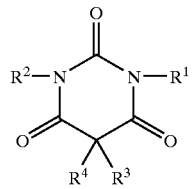

wherein $R^1$ and $R^2$ may be the same or different and are independently hydrogen;

lower alkyl, optionally substituted by lower cycloalkyl, acyl, acyloxy, aryl, aryloxy, lower alkoxy, thioalkyl or thioaryl, amino, alkylamino, dialkylamino, or one or more halogen atoms;

phenyl;

$CH_2XR^5$, wherein X is S or O and $R^5$ is lower alkyl, aryl, alkylaryl, or benzyl;

$C(O)XR^6$, wherein X is as defined above and $R^6$ is lower alkyl or aryl;

$CXR^7$, wherein X is as defined above and $R^7$ is hydrogen, lower alkyl or aryl; and $CH(XR^8)_2$, wherein X is as defined above and $R^8$ is a lower alkyl group, with the proviso that at least one of $R^1$ and $R^2$ is not hydrogen; and wherein $R^3$ and $R^4$ may be the same or different and are independently hydrogen;

aryl optionally containing one or more heteroatoms selected from the group consisting of N, S, and O;

lower acyloxy;

phenyl;

phenyl substituted with a halogen, lower alkyl group, lower acyl group or derivative thereof or acetamide;

benzyl; benzyl substituted on the ring by one or more halogens, lower alkyl groups or both; cycloalkyl, which optionally contains one or more heteroatoms selected from the group consisting of N, O, and S;

lower alkyl; or lower alkyl substituted with an aromatic moiety; provided that at least one of $R^3$ and $R^4$ is an aromatic ring or an aromatic ring containing moiety, and salts thereof, with the proviso that:

when $R^1$ and or $R^2$ is methoxymethyl, $R^3$ and $R^4$ are not both phenyl, are not both phenyl substituted by lower alkyl, and are not both phenyl substituted by halogen; and when one of $R^3$ and $R^4$ is phenyl or benzyl, the other of $R^3$ and $R^4$ is not ethyl; and when at least one of $R^1$ and $R^2$ is benzyl, then when one of $R^3$ and $R^4$ is phenyl, the other of $R^3$ and $R^4$ is not allyl; and when $R^1=R^2=R^a$, where $R^a$ is alkoxymethyl or (acyloxy)methyl, then when one of $R^3$ and $R^4$ is 1-phenylethyl, the other of $R^3$ and $R^4$ is not propionyloxy; and the compound is other than a) 1-methyl-5-(1-phenylethyl)-5-propionyloxy-barbituric acid,
b) 1,3-diphenyl-5,5-(dibenzyl) barbituric acid,
c) 1,3,5-triphenyl barbituric acid, and
d) 5-benzyl-1,3-dimethyl barbituric acid; and wherein either (a) at least one of $R^1$ and $R^2$ is lower alkyl substituted by lower cycloalkyl, acyl, acyloxy, aryl, aryloxy, thioalkyl or thioaryl, amino, alkylamino, dialkylamino, or one or more halogen atoms;

phenyl;

$CH_2SR^5$, wherein $R^5$ is lower alkyl, aryl, alkylaryl, or benzyl;

$C(S)XR^6$, wherein X is S or O and $R^6$ is lower alkyl or aryl;

$CSR^7$, wherein $R^7$ is hydrogen, lower alkyl, or aryl; and $CH(SR^8)_2$, wherein $R^8$ is a lower alkyl group; or (b) at least one of $R^3$ and $R^4$ is lower acyloxy;

phenyl substituted with a lower acyl group or derivative thereof or acetamide; and cycloalkyl of which the ring optionally contains one or more heteroatoms selected from the group consisting of N, O, and S.

3. The pharmaceutical composition of claim 1, wherein $R^1$ and $R^2$ are the same or different and selected from the group consisting of benzyl, thiophenylmethyl, cyclopropylmethyl, 3,3,3-trifluoropropyl, and benzyloxymethyl.

4. The pharmaceutical composition of claim 1, wherein $R^3$ and $R^4$ are both aromatic rings or aromatic ring containing moieties.

5. The pharmaceutical composition of claim 1, wherein at least one of $R^3$ and $R^4$ is benzyl.

6. The pharmaceutical composition of claim 1, wherein at least one of $R^3$ and $R^4$ is selected from the group consisting of

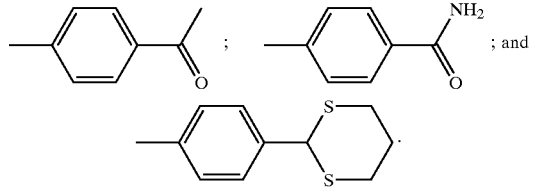

7. The pharmaceutical composition of claim 1, wherein said dose is greater than about 25 mg/kg body weight.

8. The pharmaceutical composition of claim 1, wherein said dose is sufficient to produce a blood concentration of at least 30 μg/ml of said non-sedative barbiturate or an active metabolite thereof.

9. The pharmaceutical composition of claim 8, wherein said blood concentration of said non-sedative barbiturate or active metabolite thereof is at least 30 μg/ml for at least 12 hours after said administering.

10. The pharmaceutical composition of claim 1, wherein said administered dose is greater than twice an anticonvulsant dosage.

11. A method of treating a neurological disorder comprising administering a composition according to claim 1.

12. A method of providing neuroprotection comprising (a) identifying a mammal in need of cerebral neuroprotection;

(b) selecting a pharmaceutical composition according to claim 1; and (c) administering to said mammal an effective neuroprotective dose of said pharmaceutical composition, thereby providing said neuroprotection.

13. The method of claim 12, wherein either
(a) at least one of $R^1$ and $R^2$ is
lower alkyl substituted by lower cycloalkyl, acyl, acyloxy, aryl, aryloxy, thioalkyl or thioaryl, amino, alkylamino, dialkylamino, or one or more halogen atoms;
phenyl;
$CH_2SR^5$, wherein $R^5$ is lower alkyl, aryl, alkylaryl, or benzyl;
$C(S)XR^6$, wherein X is S or O and $R^6$ is lower alkyl or aryl;
$CSR^7$, wherein $R^7$ is hydrogen, lower alkyl, or aryl; and $CH(SR^8)_2$, wherein $R^8$ is a lower alkyl group; or
(b) at least one of $R^3$ and $R^4$ is
lower acyloxy;
phenyl substituted with a lower acyl group or derivative thereof or acetamide; and
cycloalkyl of which the ring optionally contains one or more heteroatoms selected from the group consisting of N, O, and S.

14. A method of protecting a mammal from neurological damage, comprising administering to said mammal a dose of a non-sedative barbiturate, having the structure

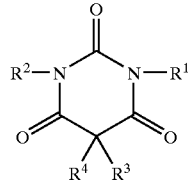

which is sufficient to provide a neuroprotective effect, said non-sedative barbiturate being non-sedative and non-hypnotic, at said dose, wherein $R^1$ and $R^2$ may be the same or different and are independently hydrogen;
lower alkyl, optionally substituted by lower cycloalkyl, acyl, acyloxy, aryl, aryloxy, lower alkoxy, thioalkyl or thioaryl, amino, alkylamino, dialkylamino, or one or more halogen atoms;
phenyl;
$CH_2XR^5$, wherein X is S or O and $R^5$ is lower alkyl, aryl, alkylaryl, or benzyl;
$C(O)XR^6$, wherein X is as defined above and $R^6$ is lower alkyl or aryl;
$CXR^7$, wherein X is as defined above and $R^7$ is hydrogen, lower alkyl or aryl; and
$CH(XR^8)_2$, wherein X is as defined above and $R^8$ is a lower alkyl group, with the proviso that at least one of $R^1$ and $R^2$ is not hydrogen; and wherein $R^3$ and $R^4$ may be the same or different and are independently hydrogen;
aryl optionally containing one or more heteroatoms selected from the group consisting of N, S, and O;
lower acyloxy;
phenyl;
phenyl substituted with a halogen, lower alkyl group, lower acyl group or derivative thereof or acetamide;
benzyl; benzyl substituted on the ring by one or more halogens, lower alkyl groups or both;
cycloalkyl, which optionally contains one or more heteroatoms selected from the group consisting of N, O, and S;
lower alkyl; or lower alkyl substituted with an aromatic moiety;
provided that at least one of $R^3$ and $R^4$ is an aromatic ring or an aromatic ring containing moiety, and salts thereof.

15. The method of claim 14, with the proviso that when $R^1$ and/or $R^2$ is methoxymethyl, $R^3$ and $R^4$ are not both phenyl, are not both phenyl substituted by lower alkyl, and are not both phenyl substituted by halogen; and
when one of $R^3$ and $R^4$ is phenyl or benzyl, the other of $R^3$ and $R^4$ is not ethyl; and
when at least one of $R^1$ and $R^2$ is benzyl, then when one of $R^3$ and $R^4$ is phenyl, the other of $R^3$ and $R^4$ is not allyl; and
when one of $R^1$ and $R^2$ is methyl and the other is hydrogen, then when one of $R^3$ and $R^4$ is phenyl, the other of $R^3$ and $R^4$ is not unsubstituted lower alkyl; and
when $R^1=R^2=R^a$, where $R^a$ is alkoxymethyl or (acyloxy)methyl, then when one of $R^3$ and $R^4$ is 1-phenylethyl, the other of $R^3$ and $R^4$ is not propionyloxy; and
the compound is other than
a) 1-methyl-5-(1-phenylethyl)-5-propionyloxy-barbituric acid,
b) 1,3-diphenyl-5,5-(dibenzyl) barbituric acid,
c) 1,3,5-triphenyl barbituric acid, and
d) 5-benzyl-1,3-dimethyl barbituric acid.

16. The method of claim 14, wherein either
(a) at least one of $R^1$ and $R^2$ is
lower alkyl substituted by lower cycloalkyl, acyl, acyloxy, aryl, aryloxy, thioalkyl or thioaryl, amino, alkylamino, dialkylamino, or one or more halogen atoms;
phenyl;
$CH_2SR^5$, wherein $R^5$ is lower alkyl, aryl, alkylaryl, or benzyl;
$C(S)XR^6$, wherein X is S or O and $R^6$ is lower alkyl or aryl;
$CSR^7$, wherein $R^7$ is hydrogen, lower alkyl, or aryl; and $CH(SR^8)_2$, wherein $R^8$ is a lower alkyl group; or
(b) at least one of $R^3$ and $R^4$ is
lower acyloxy;
phenyl substituted with a lower acyl group or derivative thereof or acetamide; and
cycloalkyl of which the ring optionally contains one or more heteroatoms selected from the group consisting of N, O, and S.

17. The method of claim 16, with the proviso that when $R^1$ and/or $R^2$ is methoxymethyl, $R^3$ and $R^4$ are not both phenyl, are not both phenyl substituted by lower alkyl, and are not both phenyl substituted by halogen; and
when one of $R^3$ and $R^4$ is phenyl or benzyl, the other of $R^3$ and $R^4$ is not ethyl; and
when at least one of $R^1$ and $R^2$ is benzyl, then when one of $R^3$ and $R^4$ is phenyl, the other of $R^3$ and $R^4$ is not allyl; and
when $R^1=R^2=R^a$, where $R^a$ is alkoxymethyl or (acyloxy)methyl, then when one of $R^3$ and $R^4$ is 1-phenylethyl, the other of $R^3$ and $R^4$ is not propionyloxy; and
the compound is other than
a) 1-methyl-5-(1-phenylethyl)-5-propionyloxy-barbituric acid,
b) 1,3-diphenyl-5,5-(dibenzyl) barbituric acid, and
c) 1,3,5-triphenyl barbituric acid.

18. The method of claim 14, wherein $R^1$ and $R^2$ are the same or different and selected from the group consisting of hydrogen, butyl, benzyl, thiophenylmethyl, cyclopropylmethyl, 3,3,3-trifluoropropyl, benzyloxymethyl, and alkoxymethyl.

19. The method of claim 15, wherein at least one of $R^1$ and $R^2$ is methoxymethyl.

20. The method of claim 14, wherein $R^3$ and $R^4$ are both aromatic rings or aromatic ring containing moieties.

21. The method of claim 14, wherein $R^3$ and $R^4$ are the same or different and are independently phenyl; phenyl substituted with a halogen or lower alkyl group; cycloalkyl, which optionally contains one or more heteroatoms selected from the group consisting of N, O, or S; benzyl; benzyl substituted on the ring by one or more halogens, lower alkyl groups or both; lower alkyl; or lower alkyl substituted with an aromatic moiety, provided that at least one of $R^3$ and $R^4$ is phenyl or substituted phenyl.

22. The method of claim 14, wherein at least one of $R^3$ and $R^4$ are selected from the group consisting of phenyl, benzyl, fluorophenyl and tolyl.

23. The method of claim 14, wherein at least one of $R^3$ and $R^4$ is selected from the group consisting of

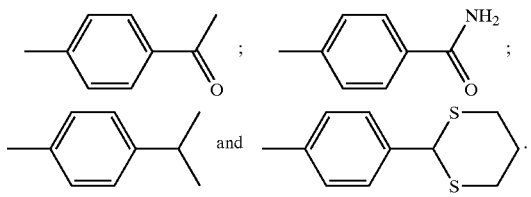

24. The method of claim 14, wherein said non-sedative barbiturate is administered in a dose is greater than about 25 mg/kg body weight.

25. The method of claim 14, wherein said non-sedative barbiturate is administered in a dose sufficient to produce a blood concentration of at least 30 μg/ml of said non-sedative barbiturate or an active metabolite thereof.

26. The method of claim 25, wherein said blood concentration of said non-sedative barbiturate or active metabolite thereof is at least 30 μg/ml for at least 12 hours after said administering.

27. The method of claim 14, wherein said non-sedative barbiturate is administered in a dose greater than twice the anticonvulsant dosage.

28. The method of claim 14, wherein said non-sedative barbiturate is administered orally or intravenously.

29. The method of claim 14, wherein said non-sedative barbiturate is administered prophylactically before evident neuronal damage or therapeutically after onset of neuronal damage.

30. The method of claim 14, wherein said non-sedative barbiturate is administered in conjunction with cardiac surgery or carotid endarterectomy.

31. The method of claim 14, wherein said non-sedative barbiturate has a neuroprotective effect that diminishes, or protects the subject from, neuronal damage caused by atrial fibrillation, a transient ischemic attack (TIA), cerebral ischemia, bacterial endocarditis, stroke, head trauma, subarachnoid hemorrhage, or other acute neurologic injury.

32. The method of claim 14, for the protection of a mammal which has or is at risk for atrial fibrillation, a transient ischemic attack (TIA), cerebral ischemia, bacterial endocarditis, stroke, head trauma, subarachnoid hemorrhage, or other acute neurologic injury.

* * * * *